(12) United States Patent
McGuinness et al.

(10) Patent No.: US 10,564,171 B2
(45) Date of Patent: Feb. 18, 2020

(54) DIAGNOSTIC CHIP (71) Applicant: Hewlett-Packard Development Company, L.P., Houston, TX (US)

(72) Inventors: Nicholas Matthew Cooper McGuinness, San Diego, CA (US); Chantelle Elizabeth Domingue, Corvallis, OR (US); Manish Giri, Corvallis, OR (US); Ed Friesen, Corvallis, OR (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 89 days.

(21) Appl. No.: 15/546,867

(22) PCT Filed: Jan. 30, 2015

(86) PCT No.: PCT/US2015/013922
§ 371 (c)(1),
(2) Date: Jul. 27, 2017

(87) PCT Pub. No.: WO2016/122643
PCT Pub. Date: Aug. 4, 2016

(65) Prior Publication Data
US 2018/0024155 A1   Jan. 25, 2018

(51) Int. Cl.
*G01N 35/00* (2006.01)
*G01N 35/08* (2006.01)
*B01L 3/00* (2006.01)

(52) U.S. Cl.
CPC ........ *G01N 35/08* (2013.01); *B01L 3/502715* (2013.01); *B01L 2200/026* (2013.01);
(Continued)

(58) Field of Classification Search
CPC ...................................................... G01N 35/08
(Continued)

(56) References Cited

U.S. PATENT DOCUMENTS 6,458,325 B1   10/2002   Roscher et al.
6,938,984 B2   9/2005   German et al.
(Continued)

FOREIGN PATENT DOCUMENTS

CN   1950504   4/2007
CN   101231285   7/2008
(Continued)

OTHER PUBLICATIONS

Yang et al. "Dielectrophoresis-Based Microfluidic Separation and Detection Systems" Int J Adv Manuf Syst. 2000 ; 3(2): 1-12. (Year: 2000).*
(Continued)

*Primary Examiner* — Christine T Mui
*Assistant Examiner* — Emily R. Berkeley
(74) *Attorney, Agent, or Firm* — Fabian VanCott (57) ABSTRACT

A microfluidic diagnostic chip may comprise a substrate, a plurality of fluidic slots extending through the substrate, a plurality of microfluidic channels each coupled to a respective one of the plurality of fluidic slots to receive a plurality of fluids from the plurality of fluidic slots, and a mixing region in fluid communication with the plurality of fluidic slots to receive the plurality of fluids such that the plurality of fluids are to mix. A diagnostic chip may comprise a number of fluid slots defined through a substrate and a plurality of microfluidic channels coupled to the fluid slots to receive from the fluid slots a plurality of different fluids wherein the microfluidic channels combine and mix the plurality of different fluids.

20 Claims, 7 Drawing Sheets

(52) U.S. Cl.
CPC ....... *B01L 2200/04* (2013.01); *B01L 2200/10* (2013.01); *B01L 2200/141* (2013.01); *B01L 2200/16* (2013.01); *B01L 2300/023* (2013.01); *B01L 2300/024* (2013.01); *B01L 2300/0627* (2013.01); *B01L 2300/0663* (2013.01); *B01L 2300/0861* (2013.01); *B01L 2300/0867* (2013.01); *B01L 2400/0406* (2013.01); *B01L 2400/0442* (2013.01)

(58) Field of Classification Search
USPC ....................................................... 422/507
See application file for complete search history.

(56) References Cited

U.S. PATENT DOCUMENTS

| | | | |
|---|---|---|---|
| 7,476,363 B2* | 1/2009 | Unger | B01L 3/5025 422/504 |
| 7,727,478 B2 | 6/2010 | Higashino et al. | |
| 2005/0129580 A1* | 6/2005 | Swinehart | B01F 5/0475 422/400 |
| 2005/0180891 A1 | 8/2005 | Webster et al. | |
| 2007/0166199 A1 | 7/2007 | Zhou et al. | |
| 2010/0165784 A1* | 7/2010 | Jovanovich | B01F 11/0045 366/163.2 |
| 2011/0005932 A1* | 1/2011 | Jovanovich | G01N 35/00029 204/453 |
| 2011/0100495 A1 | 5/2011 | Welle | |
| 2011/0287976 A1 | 11/2011 | Wang et al. | |
| 2012/0178179 A1 | 7/2012 | Kim et al. | |
| 2013/0096031 A1 | 4/2013 | Wan | |
| 2014/0030800 A1* | 1/2014 | Moses | G01N 21/64 435/288.7 |
| 2014/0241110 A1 | 8/2014 | Igata et al. | |
| 2014/0273276 A1 | 9/2014 | Fiering et al. | |
| 2014/0377145 A1* | 12/2014 | Govyadinov | B01L 3/50273 422/505 |

FOREIGN PATENT DOCUMENTS

| | | |
|---|---|---|
| CN | 101267878 | 9/2008 |
| CN | 101334419 | 12/2008 |
| CN | 101960313 | 1/2011 |
| EP | 1403518 | 3/2004 |
| JP | 2010203779 | 9/2010 |
| TW | 201100803 | 11/2011 |
| TW | 201248148 | 12/2012 |
| TW | M445178 | 1/2013 |
| TW | 201321745 | 6/2013 |
| WO | WO-2014178827 | 11/2014 |

OTHER PUBLICATIONS

Mansur et al.; A State-of-the-art Review of Mixing in Microfluidic Mixers; Chinese Journal of Chemical Engineering; vol. 16, No. 4, Apr. 14, 2008; pp. 503-516.

McGuinness et al., Microfluidic Sensing Device, Appln. No. PCT/US2014/137848; Filed Jan. 30, 2014.

* cited by examiner

DIAGNOSTIC CHIP

BACKGROUND

Infectious diseases and other medical conditions affect human life on a continual basis. Developments have been made to detect the presence of, for example, antigens in blood or other bodily fluids in order to diagnose a patient's illness. In some cases, a device is used to analyze such an analyte.

BRIEF DESCRIPTION OF THE DRAWINGS

The accompanying drawings illustrate various examples of the principles described herein and are a part of the specification. The examples do not limit the scope of the claims.

Throughout the drawings, identical reference numbers designate similar, but not necessarily identical, elements.

DETAILED DESCRIPTION

As mentioned above, certain devices may be used to analyze an analyte within a fluid. One of these devices, a microfluidic chip, may be used to help detect pathogens in the human body, for example, and diagnose an illness in a patient. A microfluidic diagnostic chip (MDC) may receive a fluid including an analyte in a fluidic slot on the MDC and analyze it for purposes of attempting to diagnose a disease in a sample from a subject or some other sample of interest. However, in some cases pathogens or other analytes in the provided sample may not be detected readily without further tests conducted in a full lab or without additional reagents to add to the sample during the analysis. The present specification therefore describes an example MDC with a plurality of fluidic slots into which a fluid including an analyte and, in one example, a reagent may be separately introduced into the MDC. Still further, the present specification describes an example of the controlled mixing of the fluids including an analyte and reagents using a number of microfluidic pumps each located in a number of microfluidic channels that the fluid and reagents are passed through. Selective activation of the number of microfluidic pumps may, for example, allow an exact ratio of fluid-to-reagents composition to be achieved and analyzed.

In one example, a microfluidic diagnostic chip may include a substrate, a plurality of fluidic slots extending through the substrate, a plurality of microfluidic channels each coupled to a respective one of the plurality of fluidic slots to receive a plurality of fluids from the plurality of fluidic slots, and a mixing region in fluid communication with the plurality of fluidic slots to receive the plurality of fluids such that the plurality of fluids are to mix. In another example, a diagnostic chip may include a number of fluid slots defined through a substrate and a plurality of microfluidic channels each coupled to a respective one of the fluid slots to receive from the fluid slots a plurality of different fluids wherein the microfluidic channels are to combine the plurality of different fluids in a combining region. In yet another example, a method of forming a microfluidic diagnostic chip may comprise forming a plurality of distinct fluid slots through a substrate, forming a plurality of microfluidic channels each fluidly coupled at their respective first ends to a respective one of the plurality of fluid slots and joining at their respective second ends in a mixing region, and forming a number of sensors within a number of the plurality of the microfluidic channels.

In the present specification and in the appended claims, the term "fluid" is meant to be understood broadly as any substance that continually deforms (flows) under an applied shear stress. In one example, a fluid includes an analyte. In another example, a fluid includes a reagent or reactant. In another example, a fluid includes an analyte and a reagent or reactant. In still another example, a fluid includes an analyte, a reagent or reactant, among others.

Additionally, in the present specification and in the appended claims the term "analyte" is meant to be understood as any substance within a fluid that may be placed in a microfluidic diagnostic chip (MDC) to be analyzed. In one example, the analyte may be any constituent substance within a fluid such as, but not limited to, animal or human blood, animal or human urine, animal or human feces, animal or human mucus, animal or human saliva, or yeast, among others.

Further, in the present specification and in the appended claims the term "pathogen" is meant to be understood as any substance that can produce a disease. In one example, the pathogen may be found in any fluid as described above.

Still further, in the present specification and in the appended claims the term "reagent" is meant to be understood as a substance or compound that is added to a system in order to bring about a chemical reaction, or added to see if a reaction occurs. A reactant is meant to be understood as a substance that is consumed in the course of a chemical reaction.

Even still further, in the present specification and in the appended claims the term "composition" is meant to be understood as either mixtures of any substance in which there is no chemical combination of components or compositions in which there is a chemical reaction between the components when they are mixed.

Additionally, as used in the present specification and in the appended claims, the term "a number of" or similar language is meant to be understood broadly as any positive number comprising 1 to infinity; zero not being a number, but the absence of a number.

In the following description, for purposes of explanation, numerous specific details are set forth in order to provide a thorough understanding of the present systems and methods. It will be apparent, however, to one skilled in the art that the present apparatus, systems and methods may be practiced without these specific details. Reference in the specification to "an example" or similar language indicates that a particular feature, structure, or characteristic described in connection with that example is included as described, but may not be included in other examples.

Figure 1:
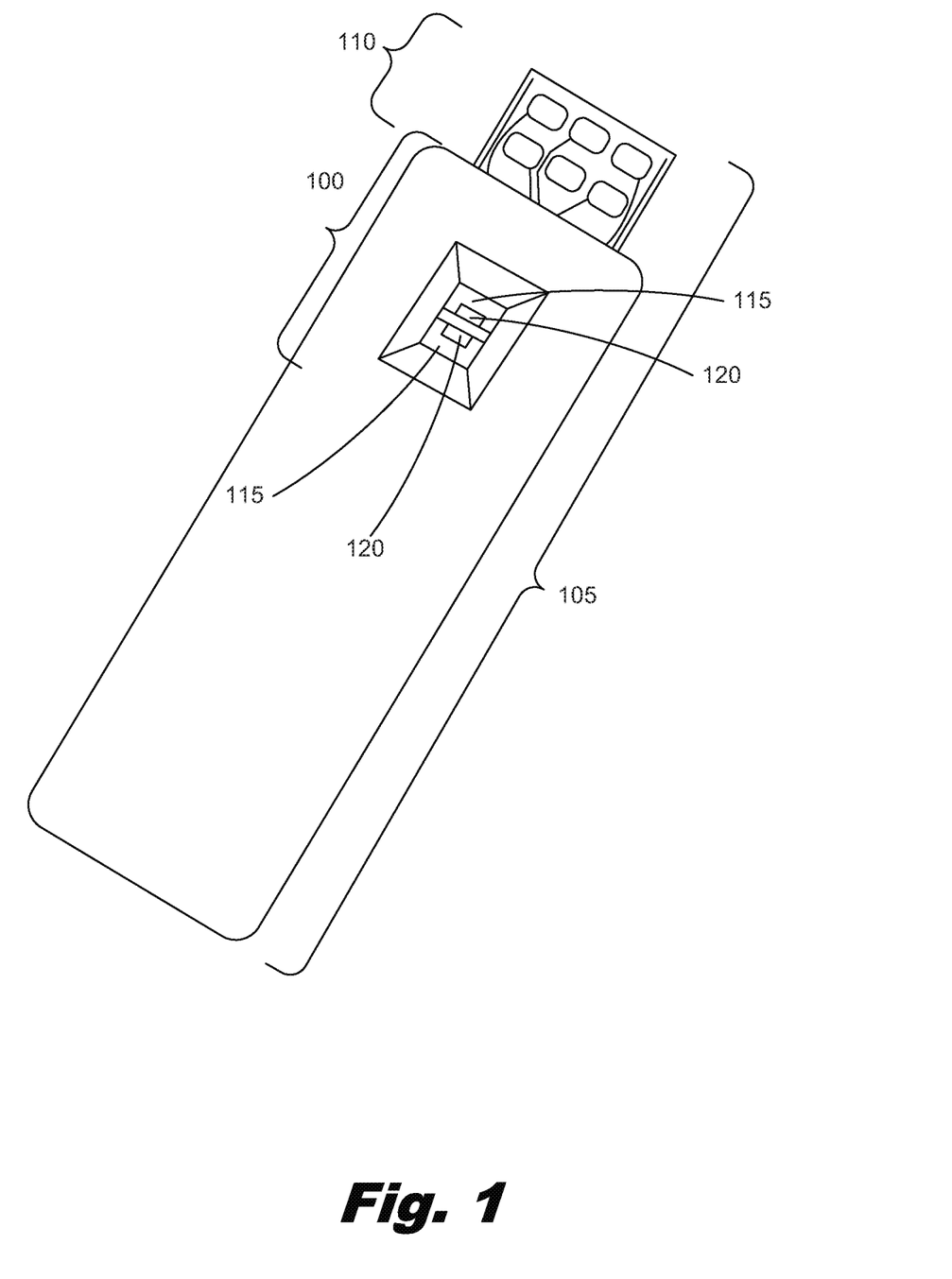
FIG. 1 is a diagram of a microfluidic diagnostic chip incorporated into a cassette for analyzing an analyte according to one example of the principles described herein.

Turning now to the figures, FIG. 1 is a diagram of a microfluidic diagnostic chip (100) incorporated into a cassette (105) for analyzing an analyte according to one example of the principles described herein. In the example shown in FIG. 1, the MDC (100) is part of the cassette (105). The cassette (105) further includes an electronic device interface (110) electrically coupled to the MDC (100). In one example, the MDC (100) may be 1 to 30 mm long and 2 to 5 mm wide. In another example, the width of the MDC (100) is approximately 2 mm wide.

The electronic device interface (110) may allow the MDC (100) to receive instructions and power from an external source such as a computing device. In this example, the MDC (100) forms the part of the cassette (105) that receives a fluid including an analyte while the cassette (105) and electronic device interface (110) provide the physical body to house the MDC and the power and instructions to operate the MDC (100) respectively.

The cassette (105) may serve as a housing into which the MDC (100) and electronic device interface (110) are housed and protected from contamination and damage. The cassette (105) may also serve as a structure onto which a user may apply pressure in order to connect the electronic device interface (110) to an electronic device, for example directly to a computing device or to a connector that can be attached to a computing device.

The electronic device interface (110) may be any electrical contact points that may interface with an input/output port of an electronic device. In one example, the electronic device interface (110) is a universal serial bus (USB) interface capable of electrically coupling to a USB port in an electronic device. In other examples, the electrical contact points of the electronic device interface (110) may be configured to fit into a PCI bus, a PCIE bus, a SAS bus, and a SATA bus, among others. In still other examples, the electronic device interface (110) may include electrical contact points that interface with a specialized port in a specialized computing device.

The MDC (100) may include a plurality of feed trays (115) into which a fluid including an analyte is placed. The feed trays (115) direct each of the fluids and reagents into a separate fluidic slot (120) of the MDC (100). During operation, a fluid including an analyte, for example, may be placed in one side of the feed tray (115) and passed into the fluidic slot (120) while a reagent, for example, is placed in a second feed tray (115) and passed into a second fluidic slot (120). The dual fluidic slot (120) in this example provides for an MDC (100) that mixes the two fluids together without those fluids having to be mixed prior to depositing them into a single fluidic slot. Although FIG. 1 shows two feed trays (115) and two fluidic slots (120), any plurality of feed trays (115) and fluidic slots (120) may be used in order to mix and analyze a number of reagents and a number of fluids including a number of analytes. Consequently, any number of compositions or sets of compositions may be made at the MDC (100) without those fluids having to be mixed prior to depositing them in the MDC (100). In one example, any one of the number of feed trays may indicate to a user via some visual identifier which fluid (i.e. fluid including an analyte, reagent, etc.) should be placed in which feed tray (115) in order to properly mix the fluids. In another example, the MDC (100) may be preloaded with reagents such that when a number of fluids including a number of analytes are placed in each feed tray (115), a different reaction may take place. In this example, the feed trays (115) may indicate which fluid is to be placed in which feed tray (115).

When the fluid including an analyte is in the fluidic slot (120) the MDC (100) may receive electrical power from an electrical device via the electronic device interface (110). The electrical power received from the electrical device may drive a number of pumps, sensors, and heaters within a number of microfluidic, channels defined in the MDC (100).

The sensors of the MDC (100) may be impedance sensors capable of measuring an impedance value of an analyte as the analyte is passed over the sensor. In one example, the impedance sensors may measure the impedance of a composition of a number of analytes and a number of reagents. The sensors may measure the impedance of the analytes and reagents before and/or after they are mixed.

The pumps of the MDC (100) may pump the fluid including a number of analytes and reagents through their respective microfluidic channels. The individual channels may vary in width depending on the type of analysis to be conducted and the type of fluids (i.e., analyte and reagents) used during the analysis. In one example, the width of the microfluidic channels may be slightly larger than the size of a single blood cell. In another example, the width of the microfluidic channels may be from 6-20 μm. In still another example, the width of the microfluidic channels may be from 1-100 μm.

The pumps may be resistors that, when a voltage is applied to them, nucleate a bubble at the surface of the thin film in contact with the fluid. This rapid Joule heating method superheats the fluid in intimate contact with a thin film resistor. The thin film resistor may be made of, for example, tantalum, platinum, gold, silicon carbide, silicon nitride, tungsten, or combinations thereof. In one example, the thin-film resistor may also include a passive film overlaying the thin film resistor and a cavitation film overlaying the passive film. The passive and cavitation film may provide thermal insulation and a physical barrier between the analyte/fluid and the thin film resistor of the microfluidic pump (210). In one example, the passive film may be made of SiC or SiN and may be approximately 500-2000 angstroms thick. In another example, the cavitation film may be made of tantalum or platinum and may be approximately 500-2000 angstroms thick.

In one example, the voltage applied may be applied at a rate of 1-100 kHz and may range from 5-35V. In other examples, the voltage may be greater that 10V or less than 5V and may be applied at different frequencies. After the fluid in contact with the resistor is superheated and the bubble is formed, the bubble collapse will occur and this nucleation and collapse event in combination with the asymmetry in the microfluidics results in a net flow of the fluid. The creation and collapse of the bubble occurs in less than 10 microseconds.

The frequency at which the resistor is heated and cooled as well as the number of pumps utilized may dictate the speed the fluids flow through the microfluidic channels. In one example, a set of 4 pumps, pumping 50 picoliters of fluid can displace 1 microliter of fluid in 1 second when operating at 5 kHz. This allows for the displacement of around 300 microliters in about 5 minutes. Additionally, as will be described in more detail below, the pumps may be selectively actuated in order to accurately mix at least two fluids in order to achieve a desired concentration of each of the analyte and reagent in the resulting composition. Because of the size of the microfluidic channels and pumps, the precision of the concentrations of the analytes and reagents may be on the nano-scale while the volume could be on the pico scale.

In one example where the fluid to be analyzed is human blood, the blood may be mixed with an anticoagulant such as ethylenediaminetetraacetic acid (EDTA). A ratio of EDTA to blood may prevent the surface of the pump or thin film resistor from foiling with blood, proteins in the blood, or other particulate that may be included in the sample of interest thereby rendering the pump non-functional. With the above composition, the pumps may continually be operated for several minutes allowing microliter volumes of blood to be analyzed.

Figure 2:
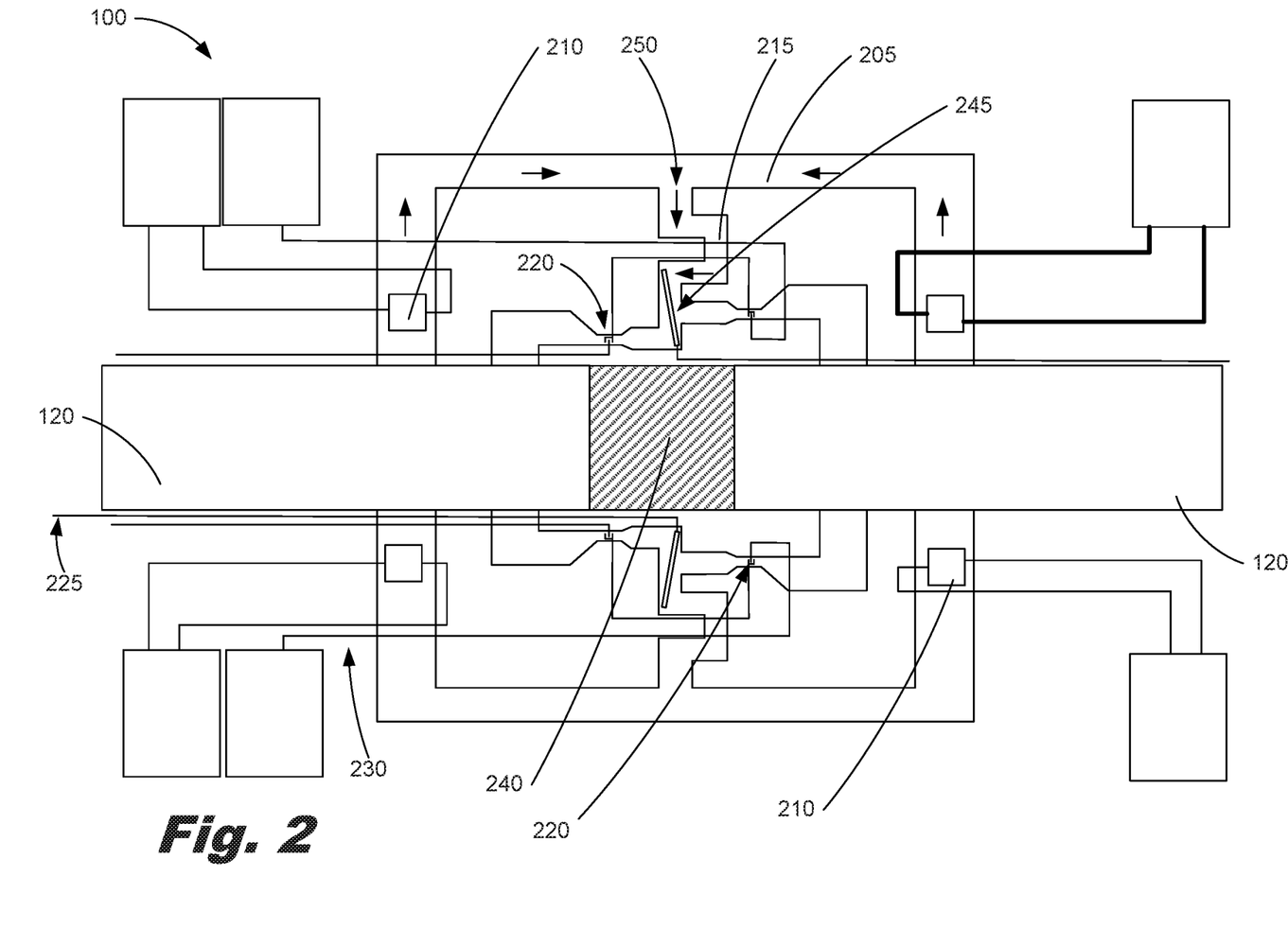
FIG. 2 is a plan view diagram of a microfluidic diagnostic chip for analyzing an analyte according to one example of the principles described herein.

FIG. 2 is a plan view diagram of a microfluidic diagnostic chip (100) for analyzing an analyte within a fluid according to one example of the principles described herein. Similar to the microfluidic diagnostic chip (MDC) (100) of FIG. 1, the plurality of fluidic slots (120) are defined in the substrate of the MDC (100) and in the example in FIG. 2 there are two. Each fluidic slot (120) is separated from each other fluidic slot (120) by a portion of the MDC (100) substrate into which the fluidic slots (120) are defined. In one example, the distance between each fluidic slot (120) may be 100 µm. The substrate rib (240) created by not removing the substrate material when defining the fluidic slots (120) in the substrate is used to fluidically separate the two fluids before they are mixed in the MDC (100). In one example, the fluidic slot (120) defined in the substrate may be 50 to 100 µm in width and 50-300 µm in length. In other examples, the number of fluidic slots (120) may be more than two as shown in FIG. 2 and, as a result, the length of the fluidic slots (120) may be shortened to accommodate the additional fluidic slots (120).

In one example, the substrate may include a silicon wafer. During operation, the fluidic slots (120) are filled up (out of the page of FIG. 2) with either a fluid including an analyte or a reagent such that they overflow into the respective microfluidic channels through capillary action.

The MDC (100) may include a number of microfluidic channels (205) with at least one microfluidic channel (205) fluidically coupled to and leading away from one of the plurality of fluidic slots (120) at a proximal end. FIG. 2 shows two microfluidic channels (205) leading away from each of the fluidic slots (120), however, the number of microfluidic channels (205) may be more or less than two and the present specification contemplates any number of microfluidic channels (205).

Each microfluidic channel (205) may comprise a microfluidic pump (210) to drive the fluid including an analyte or reagent through the microfluidic channels (205) as indicated by the arrows in the channels. As described above, the microfluidic pumps (210) may be resistors that, when a voltage is applied to them, a bubble spontaneously forms and collapses causing an inertial force that pushes/pulls the fluid through the channels (205).

Each microfluidic channel (205) leading away from a first fluidic slot (120) may be fluidly coupled at a distal end to a distal end of another microfluidic channel (205) leading away from a second fluidic slot (120). These two microfluidic channels (205) form a combined microfluidic channel (215) such that, in one example, at least one fluid including an analyte is mixed with at least one reagent. The intersection of any two microfluidic channels (205) forms a mixing region (250). The plurality of fluids may combine and mix within the mixing region (250) creating the composition. In one example, the combined microfluidic channel (215) combines a fluid with an analyte to a reagent preloaded in the MDC (100). As mentioned above, the microfluidic pumps (210) may be used to precisely control the concentrations of each of the analyte and reagent in the composition. Consequently, a number of different analyses can be made using a number of different fluids including analytes and reagents mixed at varying concentrations. Thus, one of the two pumps depicted in FIG. 2 could operate at, for example, a faster operating rate in order to mix into the composition a higher concentration of the fluid passing through the microfluidic channel (205) the pump is located in. In some examples, one of the two pumps depicted in FIG. 2 could operate at a slower operating speed in order to mix into the composition a lower concentration of the fluid passing through the microfluidic channel (205) the pump is located in. The precision of the composition may be dictated by other factors such as the length and width of each of the microfluidic channels (205) or combined microfluidic channels (215), the size of the pumps (210), the viscosity of the fluids (i.e., analytes and reagents), among others. These factors may be taken into consideration when operating the pumps so as to achieve the concentrations of the composition used during the analysis of the fluids. In one example, the length of the combined microfluidic channels (215) may be formed so as to control the length of time the analyte and reagent are mixed before being analyzed by the sensors (220).

The combined microfluidic channel (215) may comprise a number of sensors (220). The sensors (220) may be impedance sensors capable of measuring an impedance value of the fluid (i.e. analyte and reagent) composition as the composition is passed over the sensor (220). The sensors (220) may continually analyze the fluids or mixed fluids and output signals over an electrical signal connection (225) and to an electronic device via the electronic device interface (FIG. 1, 110). Each sensor (220) may therefore have both an electrical signal connection (225) and an electrical power connection (230); the electrical power connection (230) used to drive the sensor (220) and produce the signal for the electrical signal connection (225). The electrical signal connection (225) and electrical power connection (230) may be defined in the substrate during manufacture of the MDC (100).

The MDC (100) may further comprise a dielectrophoresis (DEP) separator (245). The DEP separator (245) may separate different particles within a fluid including an analyte and a reagent using a non-uniform electric field. The DEP separator (245) may direct a number of different particles down a number of microfluidic channels (205) once the analyte has been mixed with the reagent. This allows the MDC (100) to analyze a certain type of analyte within the fluid in the presence of the reagent.

The fluids analyzed in the MDC (100) may be evacuated from the MDC (100) once the fluids have been analyzed by the sensors (220). In one example each terminal end of a microfluidic or combined microfluidic channel (205, 215) may terminate as a MDC reservoir. The reservoir may be fully contained such that fluids do not leak out of the MDC (100) and cause, for example, a biohazard. In one example, a number of pumps and bores may be used to transport the fluids out of the microfluidic or combined microfluidic channels (205, 215). In another example, the fluids to be analyzed may be recirculated through the combined microfluidic channels (215) via a recirculation microfluidic channel such that the analyte and fluids may be analyzed over time.

Figure 3:
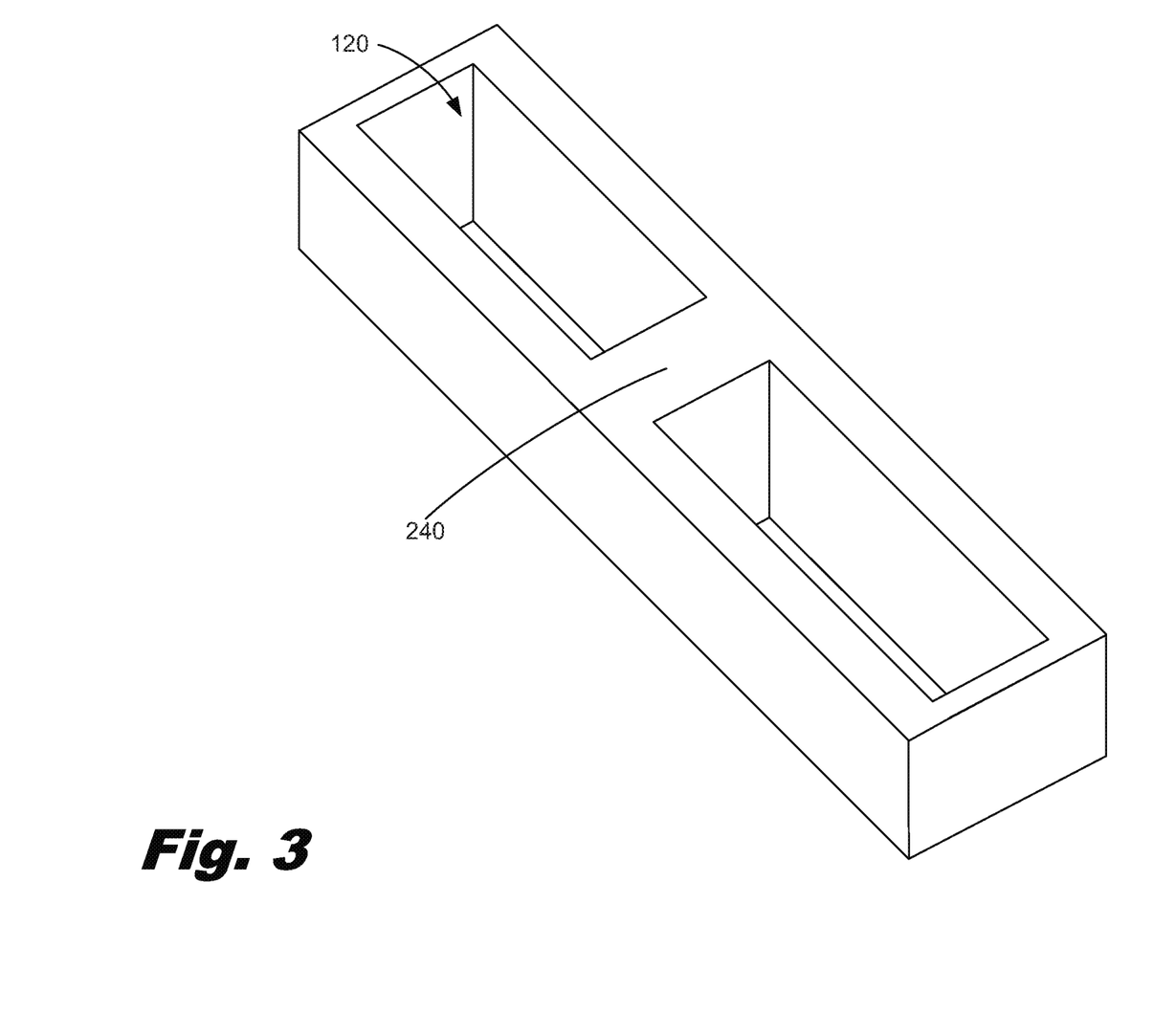
FIG. 3 is a perspective view of a fluidic slot in the microfluidic diagnostic chip according to one example of principles described herein.
Figure 4:
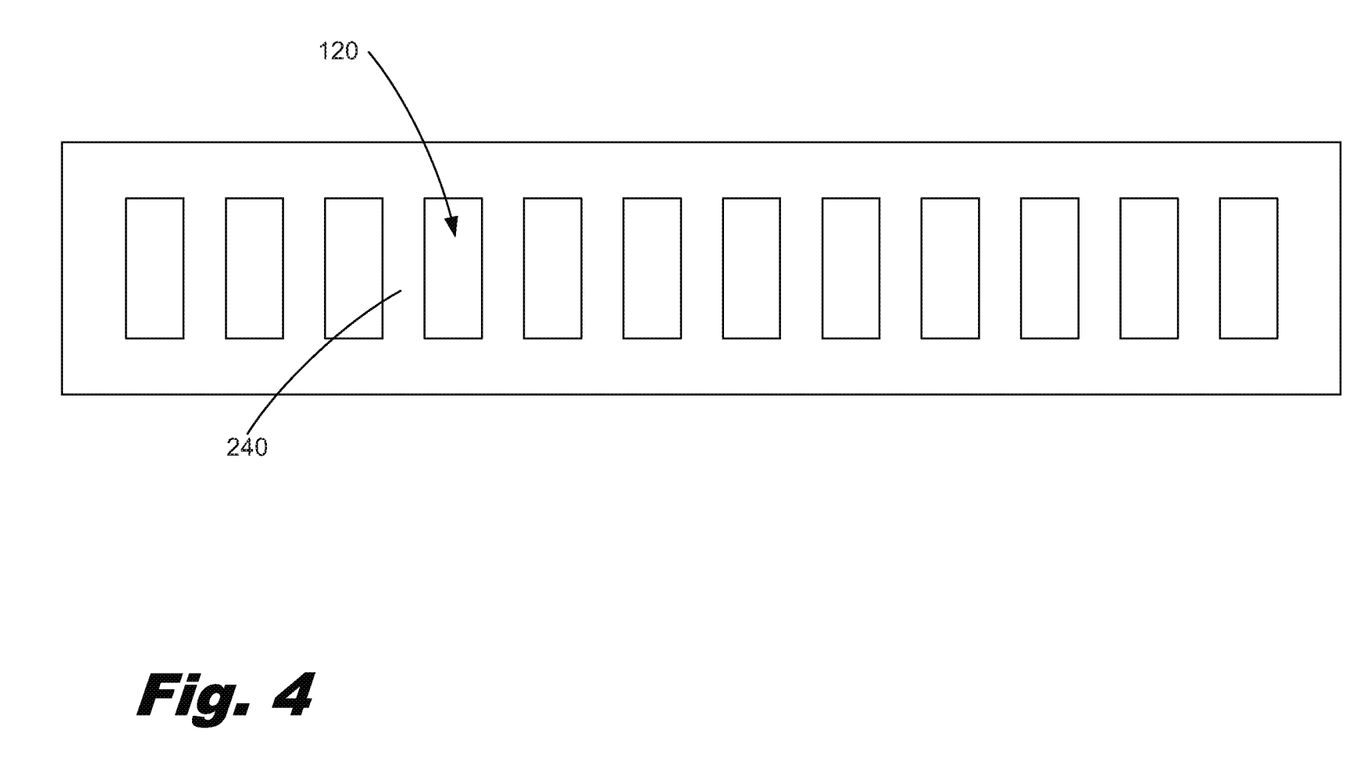
FIG. 4 is a plan view of a number of fluidic slots defined in a substrate as an array of rectangular slots according to another example of principles described herein.
Figure 5:
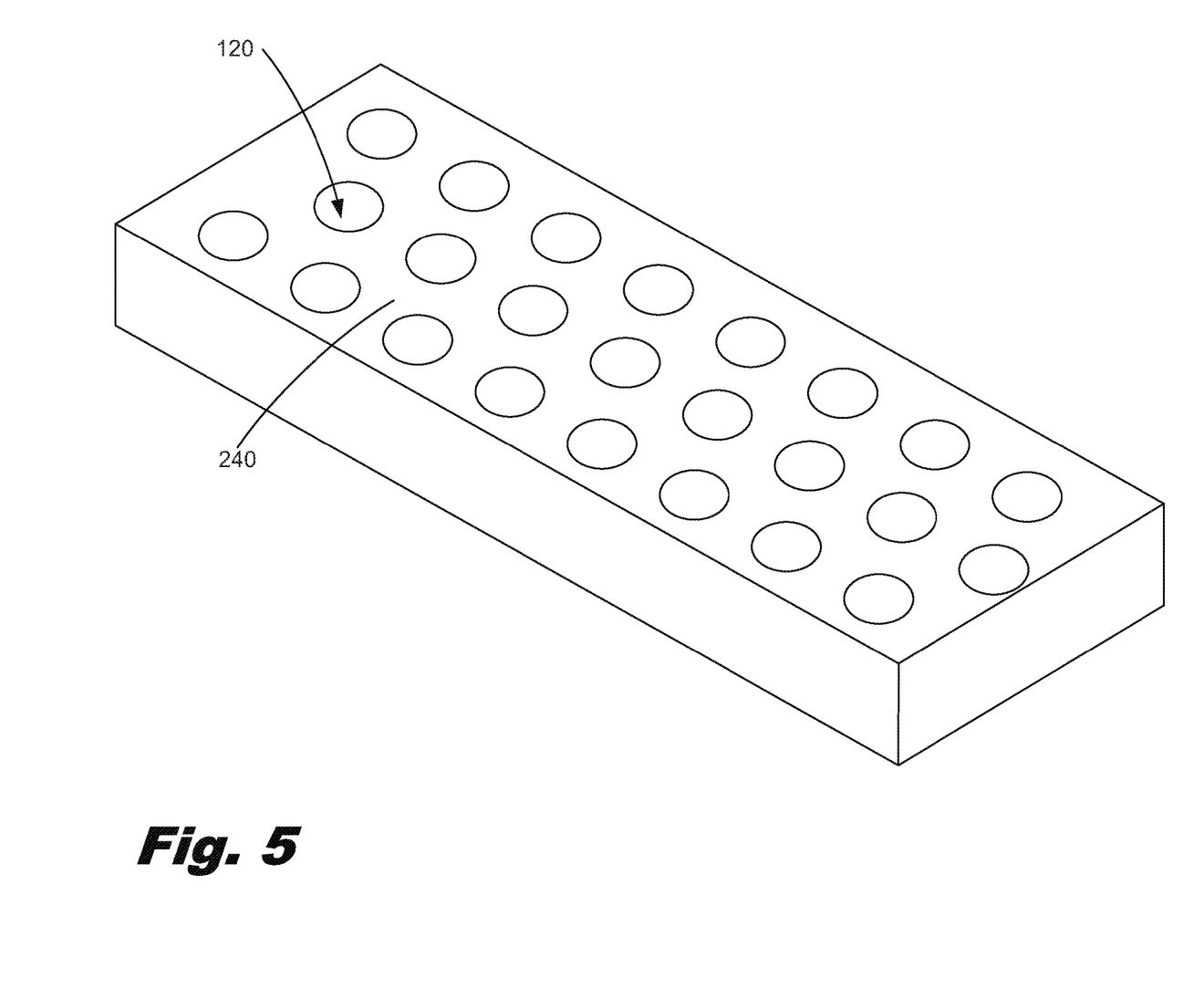
FIG. 5 is a perspective view of a number of fluidic slots defined in a substrate as an array of circular holes according to yet another example of the principles described herein.

As discussed above, the fluidic slot (120) receives a fluid therein via a feed tray (115). FIG. 3 is a perspective view of a number of fluidic slots (120) in the microfluidic diagnostic chip (FIG. 1, 100) according to one example of principles described herein. The number of fluidic slots (120) may at least be two and up to any number as dictated by the type of analysis to be conducted and the number of analytes and reagents to insert in the fluidic slots (120). FIGS. 4 and 5 further show further examples of fluidic slot (120) configurations. FIG. 4 is a plan view of a number of fluidic slots (120) defined in a substrate as an array of rectangular slots according to another example of principles described herein. FIG. 5 is a perspective view of a number of fluidic slots (120) defined in a substrate as an array of circular holes according to yet another example of the principles described herein. Each of these fluidic slots (120) are defined in the substrate by, for example, via sand blasting, laser etching, dry etching, wet etching, or combinations thereof. Additionally, as described above, each fluidic slot (120) includes a microfluidic channel (FIG. 2, 205) fluidly coupled thereto at a proximal end and connected at a distal end of the microfluidic channel (FIG. 2, 205) to the distal end of a separate microfluidic channel (FIG. 2, 205) fluidly coupled to a separate fluidic slot (120).

During operation a user may introduce any number of fluids including a number of analytes and/or reagents into one of the plurality of fluidic slots (120). In the example show in FIG. 2, a fluid including an analyte may be placed in a first fluidic slot (120) via the feed tray (FIG. 1, 115) associated with that fluidic slot (120). A reagent or other fluid to be mixed with the fluid including an analyte by adding the fluid including the reagent to a second fluidic slot (120) via the feed tray (FIG. 1, 115) associated with that fluidic slot (120). This mixing may occur in any number of fluidic slots (120) for any number of types and samples of an analyte and reagent. Consequently, multiple analyses may be made at the same time using the same device but different fluids including different analytes and reagents. Still further, in another example, multiple reagents may be mixed with a number of analytes similar to that presented in connection with FIG. 2. In this example, three fluidic slots (120) may have each of those microfluidic channels (FIG. 2, 205) associated with each fluidic slot (120) to merge and mix those fluids introduced into the fluidic slots (120). As a result, the MDC (100) described herein may provide multiple analyses on a single MDC (100) without an analyte or reagent being mixed previous to introduction into the MDC (100).

Figure 6:
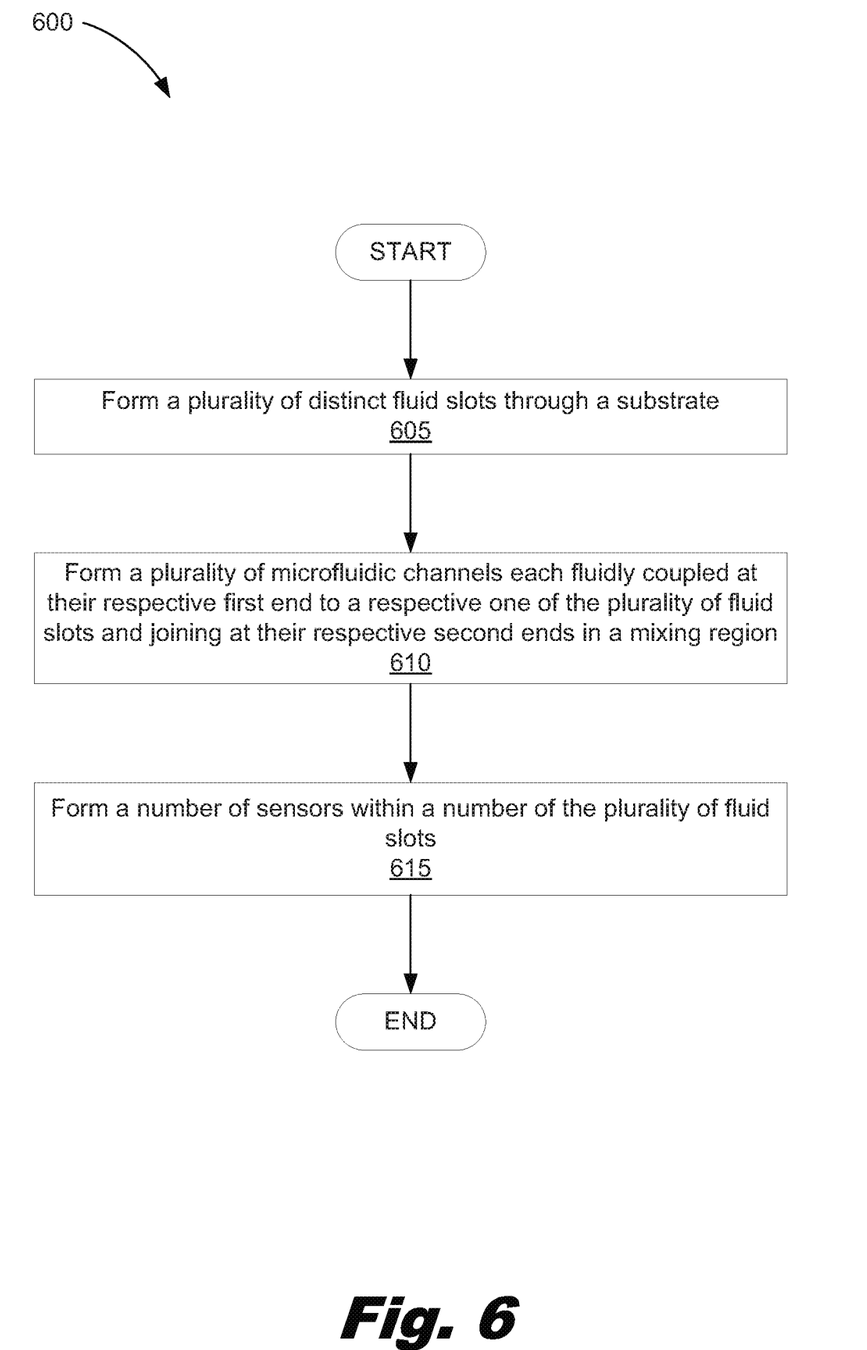
FIG. 6 is a flowchart showing a method of forming a microfluidic diagnostic chip according to one example of the principles described herein.

FIG. 6 is a flowchart showing a method (600) of forming a microfluidic diagnostic chip according to one example of the principles described herein. The method (600) may begin with forming (605) a plurality of distinct slots through a substrate. This may be done by, for example, sand blasting the substrate, laser etching the substrate, dry etching the substrate, wet etching the substrate, or combinations thereof.

The method (600) may continue with forming (610) a plurality of microfluidic channels (205) with each fluidly coupled at a first end to at least one of the plurality of fluid slots (120) and joining at a second end to at least one of the plurality of microfluidic channels (205). The microfluidic channels (205) may be joined together based on the type and number of fluids to be mixed in the MDC (100). Additionally, the microfluidic channels (205) may be defined in the substrate using, for example, a photolithography process and a material deposition process, among others.

The method (600) may further include forming (615) a number of sensors (220) within a number of the plurality of the microfluidic channels (205). The sensors (220) may also be formed by using, for example, a photolithography process and a material deposition process, among others. The sensors (220) may be electrically coupled to a power source and an electrical output line so that the sensors (220) may receive power and provide an electrical device with output during the analysis process.

Figure 7:
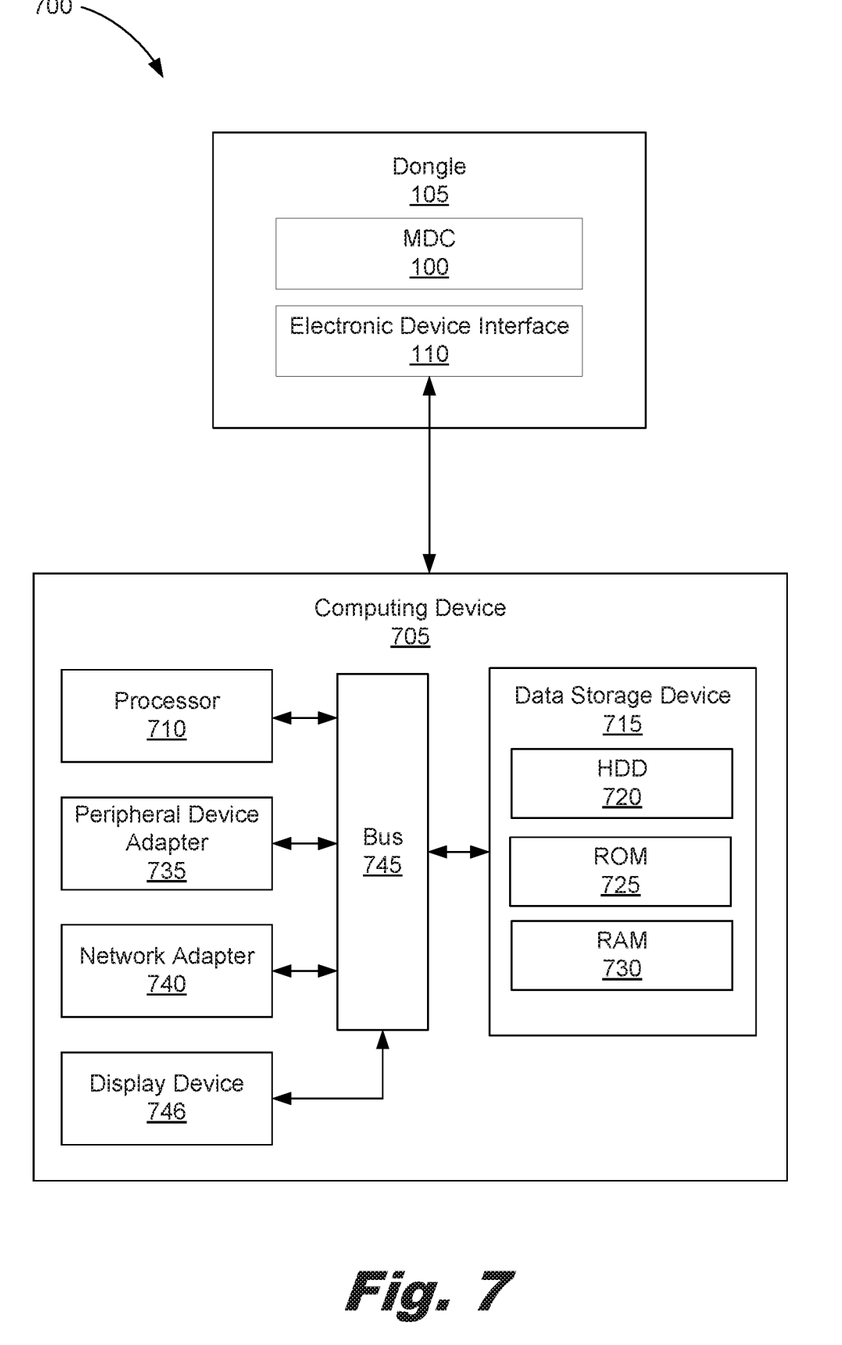
FIG. 7 is a block diagram of a microfluidic diagnostic chip system according to one example of the principles described herein.

FIG. 7 is a block diagram of a microfluidic diagnostic chip system (700) according to one example of the principles described herein. The system (700) includes a computing device (705) and a cassette (105) selectively electrically coupled to the computing device (705). The cassette (105), which may be configured as a dongle, includes a MDC (100) and an electronic device interface (110) as described above in connection with FIGS. 1 and 2. In one example, the cassette (105) may be communicatively coupled to the computing device (505) via a USB connector.

The computing device (705) includes various hardware components. Among these hardware components may be a number of processors (710), a number of data storage devices (715), a number of peripheral device adapters (735), and a number of network adapters (740). These hardware components may be interconnected through the use of a number of busses (745) and/or network connections. In one example, the processor (710), data storage device (715), peripheral device adapters (735), and network adapter (740) may be communicatively coupled via a bus (745).

The processor (710) may include the hardware architecture to retrieve executable code from the data storage device (715) and execute the executable code. The executable code may, when executed by the processor (710), cause the processor (710) to implement at least the functionality of receiving a number of electrical signals from the MDC (100) via the electronic device interface (110) and the peripheral device adapter (735), according to the methods of the present specification described herein. In the course of executing code, the processor (710) may receive input from and provide output to a number of the remaining hardware units.

The data storage device (715) may store data such as executable program code that is executed by the processor (710) or other processing device. As will be discussed, the data storage device (710) may specifically store computer code representing a number of applications that the processor (710) executes to implement at least the functionality described herein.

The data storage device (715) may include various types of memory modules, including volatile and nonvolatile memory. For example, the data storage device (715) of the present example includes Random Access Memory (RAM) (730), Read Only Memory (ROM) (725), and Hard Disk Drive (HDD) memory (720). Many other types of memory may also be utilized, and the present specification contemplates the use of many varying type(s) of memory in the data storage device (715) as may suit a particular application of the principles described herein. In certain examples, different types of memory in the data storage device (715) may be used for different data storage needs. For example, in certain examples the processor (710) may boot from Read Only Memory (ROM) (725), maintain nonvolatile storage in the Hard Disk Drive (HDD) memory (720), and execute program code stored in Random Access Memory (RAM) (730).

Generally, the data storage device (715) may comprise a computer readable medium, a computer readable storage medium, or a non-transitory computer readable medium, among others. For example, the data storage device (715) may be, but not limited to, an electronic, magnetic, optical, electromagnetic, infrared, or semiconductor system, apparatus, or device, or any suitable combination of the foregoing. More specific examples of the computer readable storage medium may include, for example, the following: an electrical connection having a number of wires, a portable computer diskette, a hard disk, a random access memory (RAM), a read-only memory (ROM), an erasable programmable read-only memory (EPROM or Flash memory), a portable compact disc read-only memory (CD-ROM), an optical storage device, a magnetic storage device, or any suitable combination of the foregoing. In the context of this document, a computer readable storage medium may be any tangible medium that can contain, or store computer usable program code for use by or in connection with an instruction execution system, apparatus, or device. In another example, a computer readable storage medium may be any non-transitory medium that can contain, or store a program for use by or in connection with an instruction execution system, apparatus, or device.

The hardware adapters (103, 104) in the computing device (705) enable the processor (710) to interface with various other hardware elements, external and internal to the computing device (710). For example, the peripheral device adapters (735) may provide an interface to input/output devices, such as, for example, display device (746), a mouse, or a keyboard. The peripheral device adapters (735) may also provide access to other external devices such as an external storage device, a number of network devices such as, for example, servers, switches, and routers, client devices, other types of computing devices, and combinations thereof.

The display device (746) may be provided to allow a user of the computing device 705 to interact with and implement the functionality of the computing device 705. The peripheral device adapters (735) may also create an interface between the processor (710) and the display device (746), a printer, or other media output devices. The network adapter (740) may provide an interface to other computing devices within, for example, a network, thereby enabling the transmission of data between the computing device 705 and other devices located within the network.

The specification and figures describe a microfluidic diagnostic chip. This diagnostic chip may, in some examples, provide a point-of-care diagnosis of an illness a patient is suffering. Additionally, the MDC may, in some examples, provide for mixing of a fluid including an analyte and a reagent in the chip without first having to measure and mix those fluids and reagents before placing them in the chip. Still further, the composition of the fluids and consequently the analyte and reagents may, in some examples, be controlled on the microfluidic level by implementing a number of microfluidic, pumps within the microfluidic channels such that pico-liters of the reagents and fluids including a number of analytes can be mixed together under a controlled manner. These exact ratios of analytes and reagents as a composition may, in some examples, be delivered to a sensor in order to better analyze the composition. Additionally, the duration that the analyte and reagents are mixed may be controlled such that the composition of the two may be analyzed by the sensors at a predetermined time.

The preceding description has been presented to illustrate and describe examples of the principles described. This description is not intended to be exhaustive or to limit these principles to any precise form disclosed. Many modifications and variations are possible in light of the above teaching.

What is claimed is:

1. A microfluidic diagnostic chip, comprising:
   a substrate;
   a plurality of fluidic slots extending through the substrate;
   a plurality of microfluidic channels each coupled to one of the plurality of fluidic slots, each microfluidic channel to receive a fluid from one of the plurality of fluidic slots;
   a mixing region in fluid communication with a plurality of the microfluidic channels, the mixing region to receive a plurality of fluids via the plurality of microfluidic channels such that the plurality of fluids are to mix; and
   a fluidic micropump disposed in each of the microfluidic channels, the fluidic mircopumps to cooperate to provide a predetermined ratio of the plurality of fluids to the mixing region.

2. The microfluidic diagnostic chip of claim 1, wherein each micropump comprises a resistor to repeatedly nucleate and collapse bubbles in a fluid in the corresponding microfluidic channel at a rate to provide the predetermined ratio of the plurality of fluids to the mixing region.

3. The microfluidic diagnostic chip of claim 2, wherein the micropumps comprise a thin film resistor separated from fluid in the corresponding microfluidic channel by a thermal insulation film.

4. The microfluidic diagnostic chip of claim 1, wherein a number of the plurality of microfluidic channels comprise a number of sensors to detect properties of the fluids.

5. The microfluidic diagnostic chip of claim 4, wherein the number of sensors are to detect the properties of the fluids before mixing.

6. The microfluidic diagnostic chip of claim 4, wherein the number of sensors are to detect the properties of the fluids after mixing.

7. The microfluidic diagnostic chip of claim 4, wherein the number of sensors are to detect impedance values of the fluids.

8. A diagnostic chip, comprising:
   a number of fluid slots defined through a substrate; and
   a plurality of microfluidic channels each coupled to a respective one of the fluid slots to receive from the fluid slot one of a plurality of different fluids;
   wherein the microfluidic channels are to combine the plurality of different fluids in a combining region; and
   a dielectrophoresis (DEP) separator at the combining region to direct different particles in the combined plurality of fluids in different directions to a number of sensors of the diagnostic chip using a non-uniform electric field.

9. The diagnostic chip of claim 8, wherein each of the plurality of microfluidic channels comprise at least one micropump that comprises a resistor to repeatedly nucleate and collapse bubbles in a fluid in the corresponding microfluidic channel.

10. The diagnostic chip of claim 9, wherein the micropumps cooperate to combine a predetermined ratio of the plurality of fluids to produce a specified composition of the plurality of fluids.

11. The diagnostic chip of claim 8, wherein a number of the plurality of microfluidic channels comprise a number of sensors to detect properties of the fluids.

12. The diagnostic chip of claim 8, wherein the microfluidic channels are fluidly coupled to an uppermost level of the fluid slots defined in the substrate.

13. The diagnostic chip of claim 8, wherein each sensor is electrically coupled to an electrode of a Universal Serial Bus (USB) connector for coupling the diagnostic chip to a computing device.

14. A method of forming the microfluidic diagnostic chip of claim 1, comprising:

forming the plurality of distinct fluid slots through a substrate;

forming the plurality of microfluidic channels each fluidly coupled at their respective first ends to a respective one of the plurality of fluid slots and joining at their respective second ends in a mixing region; and forming a number of sensors within a number of the plurality of the microfluidic channels.

15. The method of claim 14, further comprising forming a number of microfluidic pumps within a number of the plurality of microfluidic channels.

16. The microfluidic diagnostic chip of claim 1, further comprising electrical connections to connect the micropumps with an interface for a host electronic device to control the micropumps.

17. The microfluidic diagnostic chip of claim 16, wherein the interface is a Universal Serial Bus (USB) interface.

18. The microfluidic diagnostic chip of claim 16, wherein the interface provides both power and control for the micropumps.

19. The microfluidic diagnostic chip of claim 4, wherein a length of the number of the plurality of microfluidic channels corresponds to a length of time that the plurality of fluids need to be mixed before being analyzed by the sensors.

20. The microfluidic diagnostic chip of claim 1, further comprising a dielectrophoresis (DEP) separator with the mixing region to direct different particles in the plurality of fluids to different sensors of the microfluidic diagnostic chip using a non-uniform electric field.

* * * * *